United States Patent
Samkov

(10) Patent No.: US 8,088,837 B2
(45) Date of Patent: Jan. 3, 2012

(54) CUPS OF ARTIFICIAL CARDIAC VALVE AND METHOD FOR MANUFACTURING THEREOF

(76) Inventor: Alexandr Vasilievich Samkov, Moscow (RU)

( * ) Notice: Subject to any disclaimer, the term of this patent is extended or adjusted under 35 U.S.C. 154(b) by 347 days.

(21) Appl. No.: 12/309,435

(22) PCT Filed: Nov. 15, 2006

(86) PCT No.: PCT/RU2006/000601
§ 371 (c)(1),
(2), (4) Date: Apr. 9, 2009

(87) PCT Pub. No.: WO2008/010742
PCT Pub. Date: Jan. 24, 2008

(65) Prior Publication Data
US 2009/0326094 A1 Dec. 31, 2009

(30) Foreign Application Priority Data
Jul. 20, 2006 (RU) ............................... 2006126142

(51) Int. Cl.
*A61F 2/24* (2006.01)
*B29C 33/40* (2006.01)
*C08G 69/48* (2006.01)

(52) U.S. Cl. ....... 523/113; 623/2.42; 623/926; 264/219; 525/420

(58) Field of Classification Search ................ 523/113; 623/2.42, 926; 264/219; 525/420
See application file for complete search history.

(56) References Cited

U.S. PATENT DOCUMENTS
6,500,148 B1 * 12/2002 Pinchuk et al. .......... 604/103.11
2006/0195186 A1 * 8/2006 Drews et al. ................ 623/2.38
* cited by examiner

*Primary Examiner* — Michael Pepitone
(74) *Attorney, Agent, or Firm* — Aleksandr Smushkovich

(57) ABSTRACT

The invention relates to medical technology and could be used in manufacturing artificial cardiac valves having one or more cusps made of a polymer composite. The method for manufacturing a cusp of an artificial cardiac valve, includes the steps of: manufacturing a casting mold, and molding a cusp from a polymer composite comprising 78 to 92% by weight of polyamide and 8 to 22% by weight of radiographic contrast medium dispersed therein. The polymer composite can comprise additionally fine acetylene black in amount of 1 to 2% by weight. The preferred radiographic contrast medium is barium sulphate. In one embodiment of the method, the casting mold is manufactured for the molding size 1 to 5% less than necessary, and the cusp is placed after molding into an anticoagulant solution and matured therein until expanding by 1 to 5%.

3 Claims, No Drawings

CUPS OF ARTIFICIAL CARDIAC VALVE AND METHOD FOR MANUFACTURING THEREOF

REFERENCES TO RELATED APPLICATIONS

This patent application is a US National Phase of PCT-RU2006-000601 based on a Russian Federation patent application RU2006126142, hereby entirely incorporated by reference.

FIELD OF THE INVENTION

The invention relates to medical technology and could be used in manufacturing artificial cardiac valves.

BACKGROUND OF THE INVENTION

Artificial cardiac valves can comprise one, two, or more cusps having paired protrusions for fastening in the valve casing. During the valve operation, the protrusions experience a maximal mechanical loading.

Known is the method for manufacturing a cusp for an artificial cardiac valve made of titanium alloy with a coating made of pyrocarbon (RU Patent No. 2012284, 1994). However, the cusp made of two-layer material does not possess sufficient reliability when operating continuously for a long period of time. Moreover, in mounting the cusp protrusions in sockets of the casing, metal-to-metal friction problems arise.

Also known is a method for manufacturing the cusp by producing the pyrocarbon layer of controllable thickness on the surface of a graphite substrate by means of: depositing it, when decomposing carbon compounds from a gaseous stream in a through-flow reactor; separating subsequently the pyrocarbon layer from the substrate; and further processing mechanically pyrocarbon in order for shaping thereof in the form of a cardiac valve cusp (U.S. Pat. No. 6,274,191, 2001). The disadvantages of the method are its long duration, labor intensity, and the mechanical processing being performed manually, particularly at the final stage.

Known are methods for manufacturing the valve cusps from materials made on a polymer base. According to SU Inventor Certificate No. 1144216, 1987, cusps are manufactured of organic-silicon rubber reinforced by threads made of the same material. The RU Patents Nos. 2057494, 1996 and 2153887, 2000, describe methods for manufacturing cusps from polyester urethane. In the first instant, the cusp material includes additionally reinforcing fabric. In the second instance, the method provides for modifying the cusp surface using the pulse plasma spraying of carbon.

All the described methods are time-consuming and expensive, and the material of the cusps made by such methods does not keep mechanical properties and hemo-compatibility for a long time, as well as does not permit for checking for a condition of the artificial cardiac valve without surgical intervention.

BRIEF DESCRIPTION OF THE INVENTION

The claimed invention enables to simplify and cheapen significantly the process for manufacturing the cusps, increase hemo-compatibility and reliability of the artificial cardiac valve in the most loaded loci, as well as enables to observe the cusp operation in X-rays.

The method for manufacturing a cusp of an artificial cardiac valve includes the steps of: manufacturing a casting mold, and subsequently molding a cusp from a polymer composite comprising 78 to 92% by weight of polyamide and 8 to 22% by weight of radiographic contrast medium dispersed therein.

Additionally, the polymer composite could comprise fine acetylene black in an amount of 1 to 2% by weight. The presence of the black in the composite polymer permits to enhance the tribo-technical characteristics of the artificial cardiac valve, especially in long-term operation thereof.

Preferably, barium sulphate ($BaSO_4$) serves as the radiographic contrast medium. However, this function could be performed by other materials: bismuth oxychloride (BiOCl), bismuth oxide ($Bi_2O_3$), basic bismuth carbonate $(BiO)_2CO_3$, etc. In the case, when the composite formulation comprises less than 8% of the radiographic contrast medium, monitoring the cusp operation in X-rays becomes substantially impossible. When there is more than 22% of the radiographic contrast medium, the cusp material resistance to alternating loads reduces to unacceptable level in a long-term operation.

Experience has shown that the polymer composite used for manufacturing the cusps of artificial cardiac valves can expand during a long-term contact with liquids, particularly blood. In this case, the cusps of the artificial cardiac valve expands in size by 1 to 5%. Such an increase in size could result in disturbances of the cusp operation and even in impaction thereof.

In order for preventing such cases, the mold for casting the cusp is manufactured for the molding size 1 to 5% less than necessary, and, after the molding step, the cusp is placed into an anticoagulant (e.g., heparin) solution and matured therein until expanding by 1 to 5%. Thus, a double result is achieved: ensuring the cusp size stability during a long-term operation, and reducing a thrombosis probability in contacting blood with the material of the artificial cardiac valve.

EXAMPLES OF IMPLEMENTATION OF THE INVENTIVE METHOD

Example 1

An initial mixture for manufacturing the cusps of an artificial cardiac valve was prepared for loading into a molding machine. The mixture was prepared by combined grinding and stirring thoroughly at the same time an 86% weight portion of polyamide and a 14% weight portion of barium sulphate. The resulted mixture was loaded into a heatable cylinder of the molding machine and heated up to 230° C. The hot melt was supercharged into the casting mold, whose surface temperature was 75° C. After 15 sec of solidification, the casting mold was opened, and the formed cusp molding was pushed out onto a soft substrate in conditions of the room temperature and normal atmospheric pressure. When the casting mold has been made thoroughly, the produced cusp required no additional size perfection and surface processing (finishing).

The cusps thus produced (without taking into account a possible subsequent expansion) are mated for each annular valve casing taking into account a dimensional tolerance in manufacturing thereof, in order for excluding an excessively tight fit of the cusp in the casing and possible impaction of the valve in case of the cusp expansion.

Example 2

The initial mixture was prepared similarly to the one in the previous example, but with addition of acetylene black. The mixture for the polymer composite comprised 80% by weight of polyamide, 18% by weight of barium sulphate, and 2% by weight of acetylene black. The casting mold was made for the molding size 2% less than necessary. The temperature of mixture prior to the supercharging into the casting mold was 240° C., the temperature of the casting mold surface was 80° C. After the solidification, the valve cusp was pushed out of the casting mold into a heparin solution heated to 38° C. and matured therein for 3 hours for expanding (swelling). The produced cusp required no additional processing prior to mounting into the casing of the artificial cardiac valve.

Producing the valve cusps by the method of casting from a polymer composite permits to sharply increase the productivity and reduce the processing cost for manufacturing the artificial cardiac valves.

The invention claimed is:

1. A method for manufacturing a cusp of an artificial cardiac valve, including the steps of:
    manufacturing a casting mold, and
    molding a cusp from a polymer composite comprising 78 to 92% by weight of polyamide and 8 to 22% by weight of radiographic contrast medium dispersed therein; wherein the polymer composite additionally comprises fine acetylene black in the amount of 1 to 2% by weight.

2. A method for manufacturing a cusp of an artificial cardiac valve, including the steps of:
    manufacturing a casting mold, and
    molding a cusp from a polymer composite comprising 78 to 92% by weight of polyamide and 8 to 22% by weight of radiographic contrast medium dispersed therein; wherein the casting mold is manufactured for the molding size of from 1 to 5% less than necessary, and, after the step of molding, the cusp is placed into an anticoagulant solution and matured therein until expanding by from 1 to 5%.

3. A cusp of an artificial cardiac valve made of a polymer material, characterized in that the cusp is made from a polymer composite comprising from 78 to 92% by weight of polyamide and from 8 to 22% by weight of radiographic contrast medium dispersed therein, wherein the polymer composite additionally comprises fine acetylene black in the amount of 1 to 2% by weight.

* * * * *